United States Patent [19]

Moore

[11] 3,972,220
[45] Aug. 3, 1976

[54] METHOD FOR TESTING THE RESILIENCE OF SOLID PARTICLES

[75] Inventor: Charles H. Moore, Lake Jackson, Tex.

[73] Assignee: The Dow Chemical Company, Midland, Mich.

[22] Filed: May 7, 1975

[21] Appl. No.: 575,271

[52] U.S. Cl. .......................... 73/7; 241/1; 427/213
[51] Int. Cl.² ............... G01N 3/56; B02C 19/06
[58] Field of Search ............ 73/7, 432 R; 427/213; 241/1

[56] References Cited
UNITED STATES PATENTS

| | | | |
|---|---|---|---|
| 2,414,439 | 1/1947 | Brandon | 73/7 |
| 2,422,179 | 6/1947 | Brewster | 73/7 X |
| 2,976,716 | 3/1961 | De Haven | 73/7 |
| 2,983,453 | 5/1961 | Bourguet et al. | 241/1 |
| 3,253,944 | 5/1966 | Wurster | 427/13 |
| 3,636,772 | 1/1972 | Bennett | 73/7 |

OTHER PUBLICATIONS

Publication "Ultra-Fine Grinding . . . Fluid Jet Pulverizers" by Dufour et al. Mining Engineering, Mar. 1952 (pp. 262–264).

Primary Examiner—Richard C. Queisser
Assistant Examiner—Daniel M. Yasich
Attorney, Agent, or Firm—V. Dean Clausen

[57] ABSTRACT

Solid particles, such as medicinal preparations, are tested for resilience in a fluidizing apparatus. The test of this invention has several applications, such as predicting abrasion loss for particles which are to be coated in a fluidized bed coating operation, estimating abrasion loss for particles during shipping, and predicting disintegration rate of particles in fluids.

3 Claims, 2 Drawing Figures

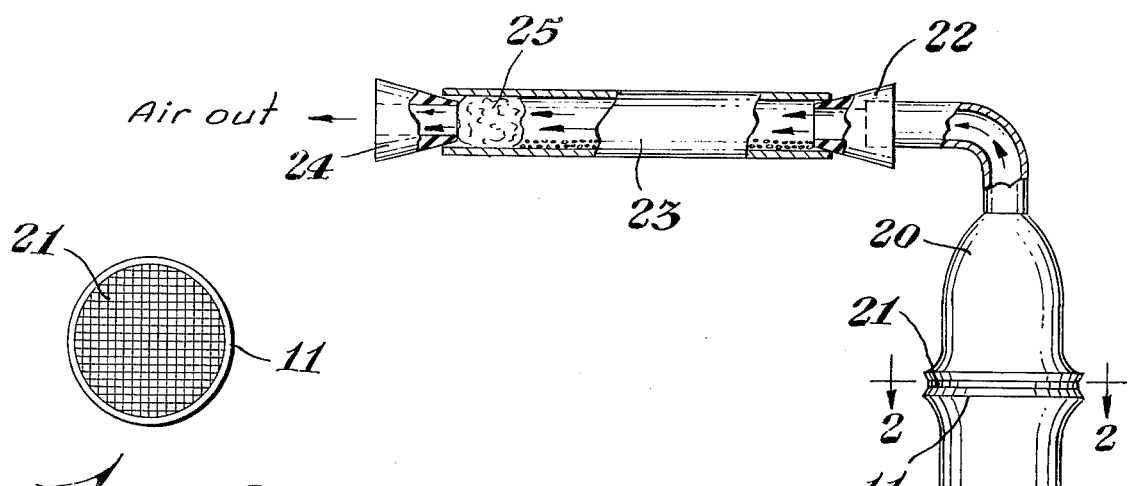
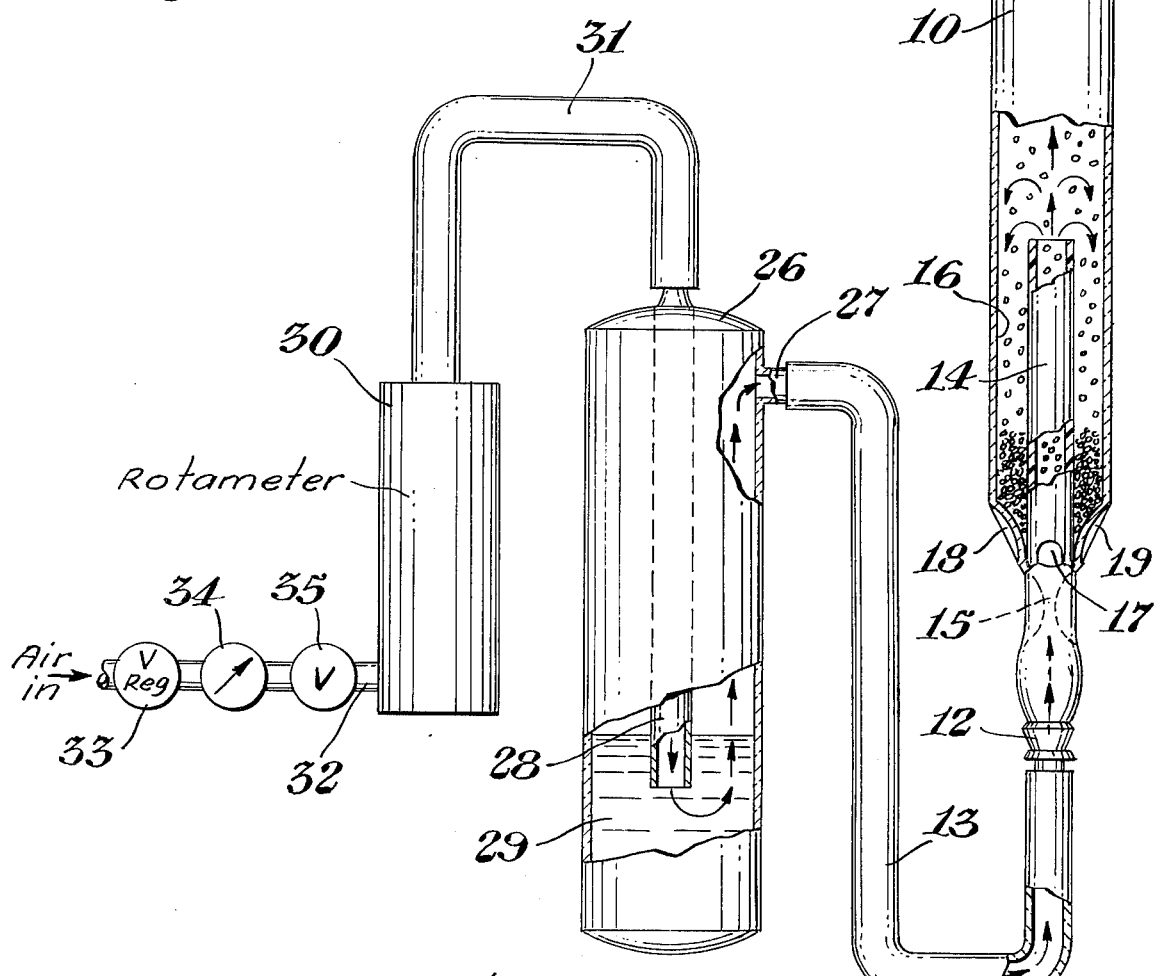

METHOD FOR TESTING THE RESILIENCE OF SOLID PARTICLES

BACKGROUND OF THE INVENTION

The invention relates broadly to a method for testing resilience of solid particles. A specific application of the invention is to provide a method for checking resilience of solid particles which are to be coated in a fluidized bed operation.

There are various chemical compositions in which the product is marketed in the form of solid particles, such as pellets or granules. In many of these formulations, such as medicinal preparations for humans or animals, the active ingredient will be contained in a base particle along with other substances such as extenders and fillers. Some of these preparations require that the base particle be coated with a material which will keep the active ingredient from dissolving in body fluids until the medicament reaches a desired point of release in the body.

A technique which is frequently used for coating the base particles is referred to as a spouting fluidized bed coating operation. In general, this technique involves placing the base particles in a hollow chamber which includes an eductor tube positioned inside the chamber. A drying gas and coating fluid are directed into the chamber through the eductor tube at a velocity which causes the particles to fluidize in the chamber. In the fluidized condition the particles will continuously recycle from the chamber upwardly through the eductor tube. This technique gets its name from the fact that during the coating operation the particles being propelled above the eductor tube resemble a spouting fluid.

For those preparations in which the base particle is to be coated in a spouting fluidized bed operation, the resilience of the particle is a significant factor to be considered. For example, during the coating operation, the particles in the coating chamber are subject to a high degree of abrasion. In this situation, if the particles have a low resilience characteristic, many of them will rupture and deform during the coating operation. The result is a substantial amount of dust particles and other particles which do not have a desirable size, and which may also have an irregular shape. It is difficult to apply a uniform coating to such particles, particularly those having an irregular shape.

Because of the situation described above, it is desirable to determine the resilience of the base particles of a formulation prior to coating the particles. One of the prior testing procedures involves placing a representative sample of the uncoated base particles on the screen of a mechanical shaker device. The uncoated particles placed on the screen are of a size suitable for coating, and the openings in the screen are usually several sizes smaller. The screen is shaken for several minutes and those particles which fall through the openings comprise the dust phase, which is unsuitable for coating. The screening test for particle resilience is not a reliable procedure. The reason for this is that the screen test does not simulate the conditions which occur when particles are coated in a fluidized bed operation.

SUMMARY OF THE INVENTION

The invention provides a method for testing the resilience of solid particles. This method has particular utility for determining resilience of particles which are to be coated in a fluidized bed operation. According to this method a bed of the solid particles is placed in a hollow vertical chamber. A stream of gas is directed into one end of the chamber at a flow rate which causes the particles to fluidize within the chamber and to continuously recycle from the chamber through an eductor tube positioned in the chamber.

Particles are held in the fluidizing condition for a period of time which will convert some of the particles to a dust phase as a result of abrasion. The gas stream propels the dust phase particles through a screen at one end of the chamber, and these particles are deposited in a collector tube which communicates with the screen. The dust phase particles in the collector tube are weighed to determine the amount of dust phase loss from the original sample.

DESCRIPTION OF THE DRAWING

FIG. 1 is an elevation view, mostly in section, of a test apparatus according to the method of this invention.

FIG. 2 is a cross section view, taken along line 2—2, of the apparatus of FIG. 1.

DESCRIPTION OF A PREFERRED EMBODIMENT

Referring to the test apparatus, as illustrated in the drawing, the numeral 10 indicates a hollow vertical chamber. The top end 11 of chamber 10 is open. The elevation view of FIG. 1 does not show the opening. The bottom end of chamber 10 tapers down to a conduit-type connector 12, in which the bottom end is open. A preferred material of construction for the chamber 10 is glass.

Positioned inside the chamber 10 is a vertical eductor tube 14. As indicated in the drawing, the tube 14 has a central lengthwise opening, so that both the top and bottom ends of the tube are open. Tube 14 also includes opposite side openings defined at the bottom edge of the tube. One of these openings is indicated by numeral 17. The lower part of the central bore in the connector piece 12 is in vertical alignment with the central opening in tube 14. The bore of connector 12 at this point defines a neck structure which provides an air passage 15. Directly above the mouth of air passage 15 the bottom edge of tube 14 adjacent to openings 17 is secured to the inner wall surface 16 of chamber 10.

The lower end of chamber 10 also includes dimple members 18 and 19, which bow inwardly toward the lower end of tube 14. The top end 11 of chamber 10 mates with the lower end of a coupling member 20. A screen member 21, as illustrated in FIG. 2, fits between the lower end of coupling 20 and the top end 11 of chamber 10. An O-ring (not shown) seats in a groove in the lip of top end 11. The O-ring thus fits against the underside of screen 21 and helps to form an air tight seal between chamber 10 and coupling 20.

Any suitable clamping means (not shown) can be used to hold the chamber 10 and coupling 20 together. In an alternative embodiment (not shown) a fritted glass structure may be fused between the coupling 20 and in chamber 10. The fritted glass member would take the place of screen 21 and would also provide means for connecting chamber 10 to coupling 20. The upper end of coupling 20 connects into the central bore of a stopper 22, which seals one end of a collector tube 23. A second stopper 24, which also has a central bore therein, seals the opposite end of collector tube 23. A glass wool plug 25 is installed inside collector tube 23 adjacent to the bore in stopper 24.

A moisture chamber 26, which communicates with chamber 10, provides means for adding humidity to the atmosphere in chamber 10. One end of an air hose 13 fits over the lower end of bottom connector 12 of chamber 10. The opposite end of hose 13 is attached to an outlet 27 at the top of chamber 26. An air delivery tube 28 is positioned vertically in the center of chamber 26. The delivery tube is open at both the upper and lower ends. In its usual operating position, the lower end of tube 28 is submerged in a body of water 29, which is contained in chamber 26.

Means for metering a gas flow (usually air) into chamber 26 is provided by a rotameter 30. The outlet of rotameter 30 is connected to the upper end of delivery tube 28 by a hose 31. A gas, such as air, from a suitable source (not shown) is directed into a bottom inlet of rotameter 30 through an inlet line 32. The pressure and flow rate of the gas is controlled by a pressure regulator 33, a pressure gauge 34, and a toggle valve 35, which are installed in line 32.

A well known feed supplement for ruminant mammals contains methionine as an active ingredient. The base particle for one such formulation would contain methionine and certain extenders and fillers. In formulating the final product the base particle is coated, in a fluidized bed coating operation, with a polymeric material. The polymeric coating is a chemical substance which prevents alkaline degradation of the methionine ingredient during ingestion of the product by the animal. As one example of the practice of this invention, the present method cna be employed to test the resilience of the methionine base particles prior to application of the coating.

The following example describes a typical test operation:

EXAMPLE

The uncoated methionine base particles have a generally spherical shape. The particles are screened to obtain a sample batch in which the average particle size is about −18/+20 mesh, or about 1 mm in diameter. The sample batch of particles, which weighs approximatey 20 grams, is placed in chamber 10. A stream of air is directed into chamber 10 at a pressure and flow rate sufficient to fluidize the particles in chamber 10. The path of the air is through regulator 33, gauge 34, valve 35, and rotameter 30. From rotameter 30 the air passes through delivery tube 28 in moisture chamber 29 and into the eductor tube 14 from air passage 15.

The air stream is maintained at a constant pressure of about 17 psig, and a constant flow rate of about 23 CFM, for a period of about 10 minutes. In practice, this pressure flow rate was found to be sufficient to maintain the particles in chamber 10 in a spouting fluidized bed condition. During the fluidizing operation the particles continuously spout upwardly through eductor tube 14, then fall downwardly in chamber 10 and reenter tube 14 through the openings 17. The dimple members 18 and 19 act as deflector plates to direct the downwardly moving particles into openings 17. Without the deflector members 18 and 19, the downwardly falling particles would hang up at the bottom of chamber 10 in the narrow annular space between inner wall surface 16 and tube 14.

As the fluidized particles recycle in chamber 10, there is a continuous abrasion between particles which generates a dust phase. The air stream carries the dust phase particles upwardly from chamber 10 through screen 21 and through coupling 20 into collector tube 23, as indicated in FIG. 1. According to the practice of this invention, the dust phase comprises those particles which are too fine to be coated. The size and the amount of the dust phase particles which are generated depends on several factors, such as the size of the base particles, and the composition of the base particles. Since the purpose of screen 21 is to permit only the dust phase particles to pass out of chamber 10, the screen size which is selected will vary according to the formulation being tested. The size of the screen used for passing the methionine dust phase particles of this example is 30 mesh (about 0.589 mm, U.S. Sieve Series).

During the 10 minute fluidizing period the air stream is continuously exhausted from collector tube 23 through the opening in stopper 24, as indicated by the arrows in FIG. 1. The purpose of glass wool plug 25 is to prevent the dust phase particles from being carried out of collector tube 23 with the air stream. Following the fluidizing period the air stream is shut off and the particles deposited in collector tube 23 and plug 25 are collected and weighed.

Before a test operation is conducted, the collector tube 23 and plug 25 must be cleaned and weighed. This enables a more accurate determination of the dust phase loss during the fluidizing operation. An average dust phase loss for the methionine formulation is about 0.10 percent by weight, based on the weight of the sample batch (20 grams). This quantity is considered an acceptable loss in a fluidized bed coating of the methionine formulation. For other formulations the acceptable dust phase loss may be a higher or a lower figure.

Certain materials of construction and various operating conditions in the method of this invention will now be described. As mentioned earlier, glass is preferred as a fabricating material for fluidizing chamber 10. Glass is also a preferred material for coupling 20, collector tube 23 and moisture chamber 26. Plastic resins are also suitable materials for these components and for the eductor tube 14. Rubber tubing or plastic resin tubing is suitable for the hoses 13 and 31.

In many fluidized bed coating operations, the drying effect of the fluidizing gas causes electrostatic charges to build up in the particle bed. If the static build-up becomes excessive a high degree of particle bridging will occur in the chamber 10. The bridging effect thus impedes normal flow of the particles in the spouting moving bed. One way to alleviate this problem is to add humidity to chamber 10 during the fluidizing operation. In the present method humidity is added to chamber 10 by water, which is entrained in the air stream as it passes through moisture chamber 26. If a method other than humidity addition is used, therefore, the moisture chamber 26 can be eliminated, and a direct connection can be made from rotameter 30 to connector piece 12.

Another operating condition of the present method is that the fluidizing gas must be compatible with the composition of the base particles which are being tested. For example, if the formulation of the particle is incompatible with air, it may be necessary to use an inert gas, such as nitrogen, As explained earlier in this description, the present method is particularly useful for determining resilience of particles which are to be coated in a fluidized bed operation. In addition, the method of this invention may be employed to predict abrasion loss which occurs in shipping of solid particles, such as granules or pellets.

In another application, it is contemplated that the present method can be utilized to predict the disintegration rate or dissolution rate of a solid medicinal preparation in a human or animal system. The reasoning here is that the resilience of a solid particle is a direct indication of the rate at which the particle will disintegrate, paticularly in a liquid medium, such as body fluids. For example, a particle made up of tightly-compacted material would be expected to dissolve or disintegrate at a slower rate than a particle containing loosely-bound material.

What is claimed is:

1. A method for testing the resilience of solid particles which are to be coated in a fluidized bed operation, the method comprising:
    placing a bed of solid particles in a hollow, vertical chamber, which has a top end and a bottom end;
    directing a stream of gas into the bottom end of the chamber and an eductor tube positioned in the chamber at controlled metered flow rate which will cause the particles to fluidize within the chamber and to continuously recycle through the chamber;
    maintaining the particles in the fluidized recycling condition for a period of time which will cause a portion of the particles to abrade to a dust phase;
    propelling only the particles in the dust phase through a screen member positioned at the top end of the chamber;
    depositing the particles which pass through the screen member in a collector tube which has been previously weighed and which communicates with the screen; and
    weighing the dust phase particles which are deposited in the collector tube after the particles are abraided and propelled through the screen member.

2. The method of claim 1 which includes adding humidity to the gas stream by passing the stream through a water chamber prior to directing the stream into the vertical chamber.

3. The method of claim 1 in which the gas stream is air.

* * * * *